(12) United States Patent
Wright et al.

(10) Patent No.: US 11,134,888 B2
(45) Date of Patent: Oct. 5, 2021

(54) SYSTEMS AND METHODS FOR SMART HOME CONTROL

(71) Applicant: Centrica PLC, Windsor (GB)

(72) Inventors: Christopher John Wright, Lausanne (CH); Julian Charles Nolan, Lausanne (CH); Timothy Giles Beard, Lausanne (CH)

(73) Assignee: Centrica PLC, Windsor (GB)

(*) Notice: Subject to any disclaimer, the term of this patent is extended or adjusted under 35 U.S.C. 154(b) by 0 days.

(21) Appl. No.: 16/659,755

(22) Filed: Oct. 22, 2019

(65) Prior Publication Data
US 2020/0121248 A1    Apr. 23, 2020

(30) Foreign Application Priority Data

Oct. 23, 2018   (GB) ..................................... 1817245

(51) Int. Cl.
| | | |
|---|---|---|
| *A61B 5/00* | (2006.01) | |
| *F24F 11/66* | (2018.01) | |
| *A61M 21/02* | (2006.01) | |
| *A61M 21/00* | (2006.01) | |

(52) U.S. Cl.
CPC .......... *A61B 5/4812* (2013.01); *A61B 5/4815* (2013.01); *A61M 21/02* (2013.01); *F24F 11/66* (2018.01); *A61M 2021/0027* (2013.01); *A61M 2021/0044* (2013.01); *A61M 2230/63* (2013.01)

(58) Field of Classification Search
CPC ........ A61B 5/4815; F24F 11/66; A61M 21/02
See application file for complete search history.

(56) References Cited

U.S. PATENT DOCUMENTS

| | | |
|---|---|---|
| 2005/0143617 A1 | 6/2005 | Auphan |
| 2011/0010014 A1 | 1/2011 | Oexman et al. |
| 2015/0238137 A1 | 8/2015 | Eyal et al. |
| (Continued) | | |

FOREIGN PATENT DOCUMENTS

| | | |
|---|---|---|
| EP | 3275494 A1 | 1/2018 |
| GB | 2550126 A | 11/2017 |

OTHER PUBLICATIONS

United Kingdom Combined Search and Examination Report, corresponding to United Kingdom Patent Application No. GB1817245.2, dated Apr. 17, 2019, Newport, South Wales, 10 pages.

(Continued)

*Primary Examiner* — Curtis B Odom
(74) *Attorney, Agent, or Firm* — Tucker Ellis LLP; Michael G. Craig

(57) ABSTRACT

A method is disclosed for controlling one or more appliances in a user environment, the one or more appliances in operation capable of causing environmental stimuli disruptive to a user's sleep. The method comprises receiving from one or more sensors data indicative of a sleep state of the user; analysing the received data to determine one or more control actions for controlling the one or more appliances to reduce sleep disruption due to the environmental stimuli caused by the appliances; and controlling the one or more appliances in dependence on the determined control actions. The method may involve determining, based on sleep state data for a first sleep period, an appliance control schedule for a second, later, time period.

19 Claims, 4 Drawing Sheets

(56) References Cited

U.S. PATENT DOCUMENTS

| | | | |
|---|---|---|---|
| 2016/0058429 A1 | 3/2016 | Shinar et al. | |
| 2016/0361515 A1* | 12/2016 | Jung | A61B 5/02055 |
| 2017/0003666 A1 | 1/2017 | Nunn et al. | |
| 2017/0213450 A1 | 7/2017 | Park et al. | |
| 2018/0073760 A1* | 3/2018 | Smith | F24F 11/66 |
| 2019/0074988 A1* | 3/2019 | Lee | A61B 5/6892 |

OTHER PUBLICATIONS

Extended European Search Report for EP Application No. 19204203.4 dated Jan. 27, 2020, 9 pages.

\* cited by examiner

SYSTEMS AND METHODS FOR SMART HOME CONTROL

CROSS-REFERENCE TO RELATED APPLICATIONS

This application claims priority to United Kingdom Patent Application No. 1817245.2, entitled SYSTEMS AND METHODS FOR SMART HOME CONTROL, filed Oct. 23, 2018, which is incorporated herein by reference.

BACKGROUND

The present disclosure relates to a control system, in particular a smart home control/scheduling system, and in particular a smart home control/scheduling system that is dependent on sleep stage and/or energy data.

Smart home control systems can automate and control connected appliances, thereby providing convenience for a user. However, automatic control of appliances may sometimes be disruptive. For example, connected appliances such as heating systems or washing machines which are controlled to run at night can disrupt the sleep quality of household occupants.

With the increasing scientific and public awareness of the importance of sleep quality, there has been a rise in consumer adoption of devices which can monitor the user's sleep stages and determine their sleep quality. For example, sleep quality tracking devices may be used to monitor a user's movement, heart rate, and/or time spent in each sleep state. Sleep stages are usually differentiated into 3 or 4 non-Rapid Eye Movement (REM) stages (N1-N3/N4) and REM, which repeat throughout a normal sleep period on an approximate 90-110 minute cycle. Each sleep stage within the cycle lasts approximately 5 to 15 minutes. Therefore, multiple deep sleep stages may occur through a sleep period, such as over the course of a night.

Sleep quality can be negatively impacted by stimuli such as sound or temperature. Furthermore, different stages of the sleep cycle are characterised by different sensitivities to stimuli, and by different optimal thermal environments. As a result, a user is affected differently by stimuli at different stages of their sleep cycle. For example, a user may have a higher sensitivity during certain sleep stages, such as during N1 "light" sleep, than during N3/N4 "deep" sleep. This results in a greater likelihood of arousal by stimuli during the lighter sleep stages than during deep sleep.

Stimuli that can disturb a user's sleep may be caused by household appliances in a smart home system. However, consumers are being incentivised and advised to run appliances at night, since electricity can be cheaper at night due to lower demand. This results in poorer sleep quality, and is becoming even further exacerbated by the trend towards smaller, more open-plan accommodation which enables sound to more easily travel throughout a property. Therefore, these problems are becoming increasingly prevalent as houses get smaller and appliances are more often run at night to save money.

In an attempt to avoid these issues, many appliances have been offered for sale which are marketed as being quiet, with the aim of allowing users to run them at night with a lesser impact on sleep quality. However, quieter appliances are often more expensive than the standard ones. Furthermore, they are still not adequate, since even low levels of noise can negatively affect sleep quality, depending on the sleep stage.

Embodiments of the present invention aim to address one or more of the above problems.

SUMMARY

In a first aspect of the invention, there is provided a computer-implemented method of controlling one or more appliances in a user environment, the one or more appliances in operation capable of causing environmental stimuli disruptive to a user's sleep, the method comprising: receiving from one or more sensors data indicative of a sleep state of the user; analysing the received data to determine one or more control actions for controlling the one or more appliances to reduce sleep disruption due to the environmental stimuli caused by the appliances; and controlling the one or more appliances in dependence on the determined control actions.

The term "appliance" as used herein includes any controllable device controllable e.g. via a wired or wireless communication interface (such as a wired or wireless computer network, Bluetooth connection etc.) The user environment may be a residential dwelling or other building or part thereof (e.g. house, apartment etc.) In typical examples, the appliances are smart home appliances adapted to interface with smart home control systems or the like. Specific examples of appliances include e.g. washing machines, dishwashers, refrigerators/freezers, lights or lighting systems, and heating, air conditioning and/or ventilation (HVAC) systems and the like.

The data indicative of a sleep state may include e.g. physiological and/or observational data relating to the user, e.g. pertaining to one or more of movement, breathing, heart rate, body temperature and the like. Analysing the sleep state may comprises determining a sleep stage classification or a progression of sleep stage classifications (e.g. based on an REM/N1/N2/N3, REM/N1/N2/N3/N4 or similar classification scheme) over a sleep period.

The method may comprise controlling the one or more appliances dynamically in response to receipt of the sensor data in dependence on a current sleep state of the user (e.g. performing control actions substantially immediately upon receipt and/or processing of the sensor data). Alternatively, the method may comprise receiving the sensor data indicative of one or more sleep states of the user over a first sleep period (e.g. a particular night); and controlling the one or more appliances based on the sensor data during a second, later sleep period (e.g. a subsequent night).

The method may comprise generating an appliance control schedule based on the received data, the control schedule specifying the one or more control actions, and controlling the one or more appliances based on the appliance control schedule, preferably wherein the sensor data is received during a first sleep period, and wherein the appliance control schedule is for controlling the appliances during a second, later sleep period.

In a further aspect of the invention (which may be combined with the previous aspect), there is provided a computer-implemented method of controlling one or more appliances in a user environment, the method comprising: receiving during a first sleep period from one or more sensors data indicative of a sleep state of the user; generating an appliance control schedule based on the received data, the control schedule relating to a second time period and specifying one or more control actions for the one or more appliances; and controlling the one or more appliances based on the appliance control schedule during the second time period.

The following features may be applied to either of the above aspects. The appliance control schedule may comprise control instructions for the one or more appliances, optionally to activate or deactivate or set an operating mode of an appliance; and/or control parameters for the one or more appliances, optionally to set an operating parameter of an appliance. Controlling the one or more appliances optionally comprises transmitting the control instructions and/or control parameters to the one or more appliances (e.g. via a network or other control interface) to cause appropriate configuration of the appliance.

The appliance control schedule preferably associates one or more control actions with a respective time at which the (each) control action is to be performed, the controlling performed in accordance with the specified times (e.g. by configuring the appliance ahead of time to perform an action at a specified time or by sending a control command to the appliance at the specified time to perform the action).

The method may comprise, based on the sensor data for the first time period, determining a sleep schedule of the user, the sleep schedule specifying a predicted sequence of sleep states over the second sleep period; and generating the appliance control schedule in dependence on the predicted sleep schedule. The sleep states may be selected from predetermined sleep stage classifications (e.g. REM, N1, N2, N3/N4) or some other appropriate classification scheme). The method may comprise analysing the sensor data to classify respective time intervals of the first sleep period into one of a predetermined set of sleep stages, and determining the predicted sleep schedule based on the classified sleep stages. The predicted sleep schedule may similarly specify a sequence of specific sleep stages, e.g. using the same classification scheme. The method may comprise analysing the sensor data to determine respective sleep state timing information (e.g. start/end and/or duration) for a plurality of sleep stages occurring during the first sleep period, and/or wherein the sleep schedule comprises respective expected sleep stage timing information (e.g. start/end and/or duration) for a plurality of sleep stages during the second sleep period. Measured and/or predicted sleep stage timings may be absolute or relative to a start of a sleep period.

The method may comprise coordinating operation of the one or more appliances with the sleep schedule, the coordinating preferably comprising selecting operation timings and/or operational parameters for one or more appliances in dependence on the sleep schedule.

Optionally, the method may comprise receiving from the sensors a plurality of data sets, each comprising sleep data indicative of sleep states of the user during a respective sleep period (e.g. respective nights during which sleep is monitored); and determining the sleep and/or appliance control schedule based on the plurality of data sets (e.g. by determining a typical, average or otherwise representative sleep schedule based on the sleep data for the plurality of sleep periods, and determining the appliance control schedule based on the representative sleep schedule).

The method may further comprise receiving environmental information relating to potentially sleep-disruptive stimuli in the user environment; receiving appliance operation information relating to operation of the one or more appliances; correlating the appliance operation information with the environmental information to identify at least one potentially sleep-disruptive stimulus associated with a given appliance; and determining the one or more control actions or control schedule in dependence on the identified stimulus.

This feature may also be provided independently. Accordingly, in a further aspect of the invention (which may be combined with any of the above aspects), there is provided a computer-implemented method of controlling one or more appliances in a user environment, comprising: receiving environmental information relating to potentially sleep-disruptive stimuli in the user environment; receiving appliance operation information relating to operation of the one or more appliances in the user environment; correlating the appliance operation information with the environmental information to identify at least one potentially sleep-disruptive stimulus associated with a given appliance; and determining one or more control actions for controlling the given appliance in dependence on the identified stimulus and optionally in dependence on sleep state data received from one or more sensors (the appliance preferably being controlled based on the determined control actions).

The following features may be applied to any of the above-described aspects of the invention.

The appliance operation information may indicate operational times of an appliance and/or may indicate times during which an appliance was operating in a particular operating mode (e.g. washing machine spin cycle). The appliance operation information may have been received from the appliance itself, from a control or monitoring system controlling or monitoring the appliance (e.g. a smart home automation/monitoring system) and/or may be derived from energy (e.g. electricity) consumption data pertaining to the appliance.

The control actions are preferably selected to counteract, reduce or eliminate the sleep-disruptive stimulus caused by the given appliance.

The control actions may comprise one or more of: deactivating an appliance, controlling a time of operation of an appliance, or controlling an operating mode of an appliance, in dependence on the received sleep state data (sensor data).

Preferably, controlling one or more appliances comprises preventing or adjusting operation of an appliance to avoid or reduce a sleep-disruptive environmental stimulus during a sleep stage identified as corresponding to a light sleep state (e.g. N1). Alternatively or additionally, controlling one or more appliances may comprise scheduling operation of an appliance producing a sleep-disruptive environmental stimulus during a sleep stage corresponding to a deep sleep state (e.g. N3 and/or N4).

The method may further comprise evaluating a sleep impact of an appliance in dependence on an environmental stimulus produced by the appliance and a current or predicted sleep stage of the user, and determining the appliance control actions or schedule in dependence on the sleep impact. Note that a current sleep stage may be used in a dynamic embodiment e.g. responding immediately to user sleep by controlling appliances, whilst predicted sleep stages of a sleep schedule may be used in a predictive embodiment where a future sleep schedule is determined based on past sleep data and used to determine an appliance control schedule for future sleep periods.

The method may comprise evaluating the sleep impact further in dependence on a determined sensitivity of the user to the stimulus. The sensitivity may e.g. be determined as a numerical measure (e.g. probability of arousal to a lighter sleep stage or to wakefulness).

The method may comprise, for one or more environmental stimuli caused by one or more appliances: detecting the environmental stimulus using one or more environmental sensors; analysing the sleep data to determine an effect of the environmental stimulus on the user sleep state, optionally by correlating detection of the environmental stimulus with changes in user sleep state; and determining a user sensitivity to the stimulus based on the analysis; the method preferably further comprising controlling the one or more appliances in dependence on the determined user sensitivity, optionally by selecting an appliance to be controlled based on the user sensitivity data and/or determining an appliance control action or schedule in dependence on the user sensitivity data.

The environmental stimuli may, for example, comprise one or more of: sound, light, and temperature.

Control actions may, for example, comprise one or more of: disabling or altering an operating mode or schedule of a noise-generating appliance to reduce noise disruption; and disabling or altering an operating mode or schedule, or modifying a target temperature or temperature control schedule, of a heating, ventilation or air conditioning (HVAC) appliance.

The method may further comprise determining the control actions or schedule further in dependence on energy consumption and/or energy cost information. In one example, the method may comprise determining an appliance control schedule by selecting appliance operation timings based on the sleep schedule and time-variable energy costs.

The method may also comprise outputting sleep schedule information to a user specifying proposed sleep adjustments to reduce sleep disruption due to appliance operation and/or allow appliance operation during times associated with reduced energy costs.

In some embodiments, the method may comprise determining an appliance control schedule using an optimisation function to determine timings of connected appliance activities given one or more of: a determined sleep schedule, one or more sleep goals, appliance stimulus data defining environmental stimuli caused by appliances, user sensitivity data indicating a user sensitivity to one or more stimuli, and energy consumption and/or energy cost data.

The invention also provides a system having means, preferably in the form of a processor with associated memory, for performing any method as set out herein, and a (tangible) computer-readable medium comprising software code adapted, when executed on a data processing apparatus, to perform any method as set out herein.

Aspects of the invention may be combined in any appropriate manner and features of one aspect may be applied to other aspects. Features described as implemented in software may be implemented in hardware and vice versa.

Advantages of the present invention will become further apparent from the detailed description and figures.

DESCRIPTION OF THE DRAWINGS

Embodiments of the present invention will now be described, by way of example only, with reference to the accompanying drawings, in which.

DETAILED DESCRIPTION

Embodiments of the invention coordinate appliance activity scheduling with user sleep stages. In doing so, they can reduce sleep disruption caused by appliance activities and/or provide energy-related benefits such as improved utilisation of low-cost electricity and load balancing in the electricity distribution grid.

Embodiments of the present invention relate to a scheduling system, such as a smart home scheduling system, and to methods for smart home scheduling.

Figure 1:
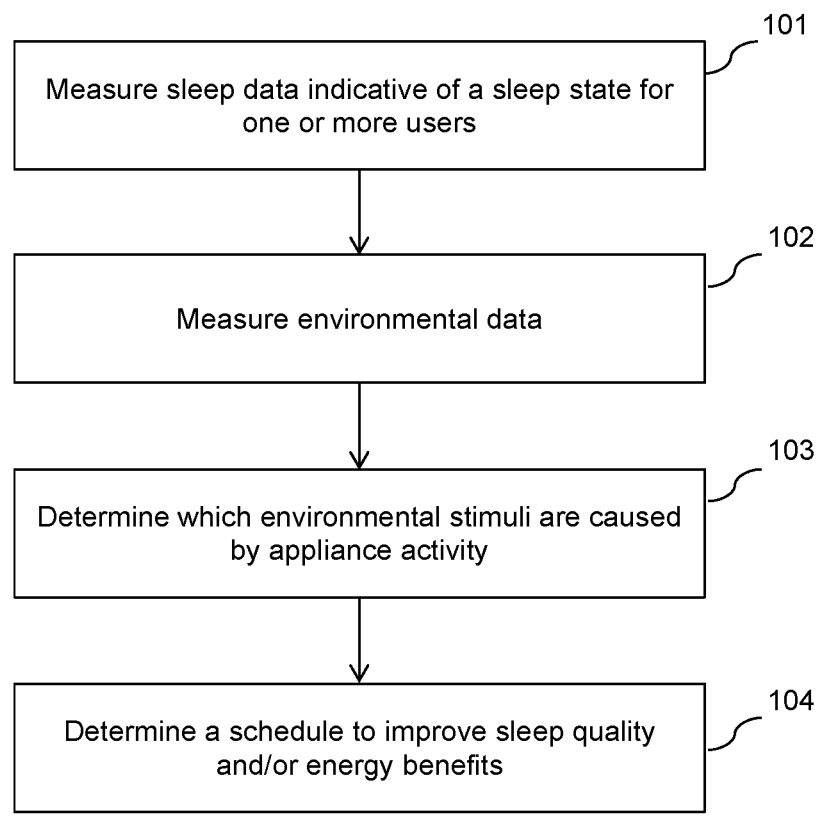
FIG. 1 illustrates in overview a method for smart home scheduling.

An overview method for smart home scheduling is shown in FIG. 1. The system measures sleep data indicative of a sleep state for one or more users (step 101). Using the sleep data, the system may predict the user's sleep schedule some time in advance of a sleep period such as a night's sleep. Preferably, the predicted sleep schedule includes predicted timings of user sleep stages.

In step 102, the scheduling system measures environmental data relating to one or more environmental factors (stimuli) that may affect the user(s). Examples of environmental factors/stimuli include sound, temperature, and/or light. The stimuli may be caused by an appliance performing an energy consuming activity.

The system also receives or measures information regarding household appliances and their activities. Using this information, the system determines in step 103 which environmental stimuli occur as a result of appliance activity. For example, this may be determined by temporally correlating environmental stimuli with appliance activity data.

Optionally, the scheduling system may determine a sensitivity for the one or more users. The sensitivity indicates how the user(s) are affected by environmental factors. A plurality of sensitivities may be determined for each user, with different sensitivities occurring in response to different types of stimuli and/or during different sleep stages. The system may determine sensitivity, for example, through analysis of user sleep data in combination with environmental data.

In step 104, the scheduling system determines one or more appliance and/or sleep schedules to improve sleep quality and/or energy benefits. The schedule may be determined predictively and/or dynamically. For example, a schedule may be determined some time in advance of the scheduled period, for instance based on the above-described predicted user sleep schedule. Alternatively or in combination, a schedule may be dynamically determined and/or updated in response to current sleep data and/or current environmental data. In embodiments which dynamically determine a schedule, the sleep schedule is not necessarily determined in advance of the scheduled period. For example, an appliance schedule may be dynamically determined/updated based on current (rather than predicted) sleep data.

Hence, embodiments of the present invention create one or more appliance and/or sleep schedules to improve the sleep quality of a user, and which can reduce energy costs and/or achieve network load balancing benefits. For example, sleep quality may be improved by creating an appliance schedule which coordinates appliance activity with user sleep stages, to manage the scheduling of appliance activities that cause potentially disruptive stimuli. Sleep disruption may be reduced by controlling disruptive appliance activities to occur during periods of deep sleep instead of light sleep. This can reduce the likelihood that the user will be disturbed or awoken by stimuli caused by the appliance activity. Furthermore, an appliance schedule may reduce energy costs by scheduling appliances to run during off-peak low priced energy periods. This may be achieved at little or no cost to sleep quality.

In addition to specifying the timing of appliance activities, an appliance schedule may optionally further control specific settings for an appliance activity. For example, an appliance schedule for a heating appliance may control the desired temperature setting as well as the timing. Furthermore, a schedule for an appliance such as a dishwasher or washing machine may specify the desired temperature and cycle. It is envisaged that the system may be able to suitably control different settings for a variety of appliances, further including but not limited to volume (e.g. of a TV or radio), brightness (e.g. of a lighting system), etc.

Optionally, some embodiments may achieve even greater energy and/or sleep benefits by monitoring and adjusting the user's sleep schedule. For example, the system may determine a sleep schedule (optionally including timing of a user's sleep stages) which improves synchronisation with periods of cheap energy, e.g. by providing a greater period of overlap between the times spent asleep and/or in a deep sleep stage, and the times during which energy pricing is lowered. For example, the user's sleep schedule may be adjusted such that some or all of the REM sleep stage is experienced during an off-peak low pricing energy period.

The system may output the resulting appliance and/or sleep schedule to a user, optionally providing options for the user to accept, reject, and/or amend the schedule. If the user rejects or amends the schedule, the system alters the schedule accordingly. In embodiments where the system determines an appliance schedule, the schedule may be transmitted to the appliance, which enacts the appliance activity at the scheduled time. Alternatively, the system may include a central controller that controls the appliance to enact the appliance activity at the scheduled time. For example, this may be achieved by the central controller transmitting a control signal to the appliance at the scheduled time.

Hence, embodiments of the invention may provide some or all of the following features:
- A system and method to determine and/or predict one or more environmental factors/stimuli which the user is exposed to as a result of appliance activities.
- A system and method to determine the user's sensitivities to stimuli during different sleep states.
- A system and method to find the optimum timing of connected appliance activities to coincide with user sleep stages, improving sleep quality and/or energy related benefits.
- A system and method to adjust an individual's sleep schedule in tandem with appliance scheduling, to further improve sleep and/or energy benefits.

Although embodiments described herein may optimise or improve sleep quality, energy cost, and load balancing, in certain alternative embodiments only one or two of these features may be optimised. That is, in some embodiments, the connected appliances may be scheduled to improve user sleep quality, without taking into account energy pricing and/or load balancing. Conversely, alternative embodiments may schedule connected appliances such that energy cost and/or load balancing are improved, without taking into account user sleep quality. It is hence envisaged that any of these factors may be improved, either alone or in combination with one or more other factor.

Figure 2:
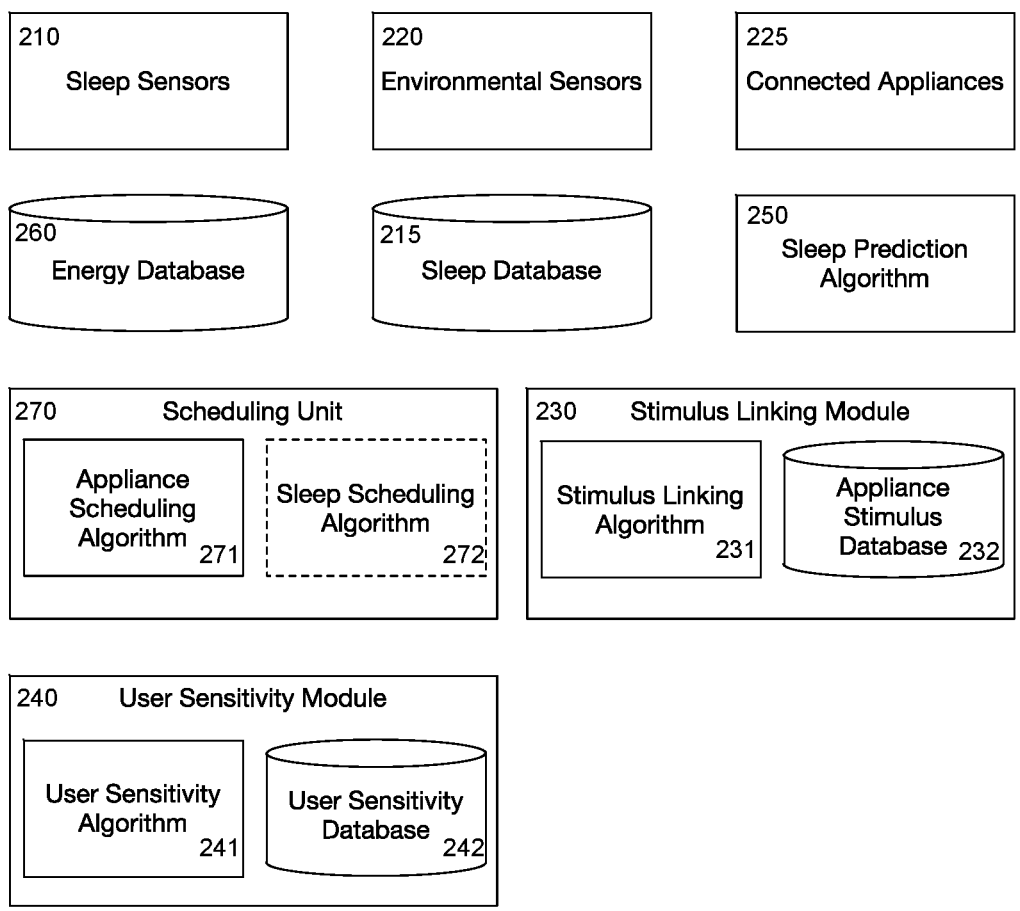
FIG. 2 illustrates a sleep stage dependent smart home control/scheduling system.

Referring to FIG. 2, there is provided a scheduling system in accordance with embodiments of the invention. The scheduling system may be a standard connected home system, also known as a smart home system, wherein devices within the system are remotely controllable and/or may be controlled by other devices within the system.

The system includes one or more sensors, hereinafter referred to as "sleep sensor(s)" 210. The sleep sensor(s) 210 are configured to measure one or more indicators of the user's sleep state, such as the user's movement, sound, respiration, heart rate, and/or any other user properties which may be affected by and/or indicative of sleep state. The sleep sensor(s) 210 further comprise (or are connected to) processing means for processing the indicators in order to determine the user's sleep state and/or the time spent within one or more sleep stages N1 to N4 and REM.

The sleep state and/or indicators of the sleep state are stored as sleep data in a sleep database 215. The sleep database 215 is configured to store the sleep data for a single user or multiple users over a period involving at least one sleep period, for example over multiple nights. The one or more sleep sensors 210 may have a memory comprising the sleep database 215, and/or may have communication means for transmitting the sleep data to a separate module comprising the sleep database 215.

The sleep sensor(s) 210 may be configured to record and/or store sleep data automatically, or may be manually activated by a user. Examples of sleep sensors 210 include a smart mattress, a smartphone with a sleep monitoring app, a wearable sensor with sleep monitoring capabilities such as a fitness band or smart watch (e.g. Fitbit™), and/or in-room connected sensors capable of sleep monitoring, such as motion-detectors, cameras and/or microphones. For example, user motion or breathing may be detected using optical/infrared image information from an optical or infrared camera or sensor, or using accelerometers or other motion sensors, whilst heart rate may be detected using an infrared sensor in contact with the user's body (as commonly used in smart watches or the like). Other types of sleep sensor(s) 210 may also be used which are not mentioned herein. Furthermore, any sleep sensor 210 may be used alone or in combination with another sleep sensor 210 or type of sleep sensor 210. For example, multiple sensors may be used to collect different types of sleep data, and/or to provide a larger sample size and thus improve data reliability compared to having fewer sensors or a single sensor.

The system may further include one or more environmental sensors 220 to monitor the environmental conditions which the user, or sleep location, is exposed to. The environmental sensor(s) 220 may be positioned in the room where the user sleeps, or may be otherwise configured to record environmental data relating to environmental stimuli which affect the conditions at the sleep location, e.g. by measuring the environmental stimuli at/near the connected appliance itself.

The one or more environmental sensors 220 produce environmental data such as data relating to temperature, light levels, sound volume, and/or sound frequency values. A database for storing the environmental data may be included in the environmental sensor(s) 220 or may be part of another component of the system.

In some embodiments, an environmental sensor 220 may be a smartphone placed on or near the user or sleep location, such as on a bedside table, wherein the smartphone has an app for measuring one or more environmental factors. In some embodiments, an environmental sensor 220 may be a thermometer and/or microphone, optionally connected to one another.

The system further includes one or more connected appliances 225 which perform energy consuming functions, referred to herein as connected appliance activities. Examples of connected appliances include (but are not limited to) a washing machine, a heating system, a lighting system, a dishwasher, and a fridge-freezer, such as a fridge-freezer with a compressor, and other examples described herein. The one or more connected appliances 225 may be controllable to some extent through network connections, for example through connections in the smart home system. Connected appliance activities may cause environmental conditions which the user or sleep location is exposed to, and hence may affect the user's sleep, for example through noise produced, light emitted, and/or temperature. Hence, the one or more environmental sensors 220 can measure environmental conditions that are caused by the one or more connected appliances 225 performing connected appliance activities.

Information relating to a connected appliance's performance of connected appliance activities may be provided either by the connected appliance 225 itself and/or by another appliance, which may or may not itself be a connected appliance 225. This information is represented by appliance activity data.

The system further includes a stimulus linking module 230 configured to determine the environmental data which corresponds to (and is caused by) each connected appliance activity. The stimulus linking module 230 has a stimulus linking algorithm 231 configured to use appliance activity data in order to extract the components of the environmental data which are caused by each connected appliance activity. For example, this may be achieved by temporally matching environmental data with time-corresponding appliance activity data. Alternatively or in combination, the system may include an environmental sensor (e.g. a microphone) near the connected appliance. The stimulus linking algorithm 231 may then correlate environmental data measured near the connected appliance with environmental data measured near the user location (e.g. by measuring sound near an appliance and correlating this with the sound at the user location).

The extracted components, hereby referred to as appliance stimulus data, may be in the form of an exact, average or possible range of environmental data which is associated with each defined connected appliance activity. Appliance stimulus data may therefore comprise an environmental condition such as an audio, thermal, or visual condition that varies over time and is associated with each connected appliance activity.

Properties of the house/dwelling itself may affect the efficiency with which environmental conditions propagate from a connected appliance to a user. The propagation of environmental characteristics such as sound or heat may be modelled using a transfer function specific to the property. The stimulus linking algorithm 231 may optionally take into account house state data that is related to the transfer function(s) of the house or dwelling where the user sleeps.

The appliance stimulus data may contain one or more additional subcategories for each connected appliance activity, wherein each subcategory relates to a possible transfer function such as an acoustic transfer function, a light transfer function, or a temperature transfer function. For example, a transfer function may take into account the composition and/or thickness of walls, doors, and floors; whether any doors are open between an appliance and a user; the distance between a user and an appliance; and how full/empty the dwelling is.

The stimulus linking module 230 may further include, or be connected to, an appliance stimulus database 232 configured to store appliance stimulus data.

The system may optionally include a user sensitivity module 240 configured to determine the sensitivity of one or more users to different stimuli during one or more sleep states. The user sensitivity module 240 comprises a user sensitivity algorithm 241. The user sensitivity algorithm 241 uses environmental data and sleep data to determine the effect of one or more stimuli on the sleep data of the user, thereby indicating the user's sensitivity during one or more sleep states. The output of this algorithm is referred to as user sensitivity data. User sensitivity data may comprise a table of defined effects on sleep (such as arousal to a lighter sleep state and the corresponding likelihood of occurrence) which are associated with different combinations of current sleep states and identified stimuli categories. Other relevant information categories that may significantly affect the likelihood of arousal may also be included in the table. Multiple subdivisions of stimuli categories may be chosen, such as different sound frequency bands and amplitude bands. To reduce the number of categories and/or subdivisions which may be required, categories may be chosen based on appliance stimulus data.

The user sensitivity module 240 may further include (or be connected to) a user sensitivity database 242 configured to store the user sensitivity data.

The system further includes a sleep prediction algorithm 250 configured to predict the sleep schedule of the user, preferably including the different sleep states and their likely timing (e.g. the sleep schedule may specify start times and end times or durations for each detected sleep state, together with measured characteristics of the sleep state and/or a sleep state identifier or label such as REM/N1/N2/N3/N4). The resulting data, referred to herein as sleep schedule data, is determined by using sleep data and optionally any other factors which may affect the dynamics of the user's sleep.

In some embodiments, an energy database 260 configured to store energy data is also provided. Energy data may comprise information provided by an energy management body such as an energy supplier regarding predicted and/or known energy pricing and/or load balancing concerns some time into the future. Also included in the energy data may be the pre-calculated energy cost of each connected appliance activity, which may be adjusted for different energy prices which occur at different times.

The system further includes a scheduling unit 270 configured to determine an appliance and/or sleep schedule some time in advance. The schedule(s) may be created to optimise sleep benefits and/or energy related benefits. For example, the schedule(s) may optimise sleep quality, electricity cost, and/or load balancing, either alone or in combination.

The scheduling unit 270 includes an appliance scheduling algorithm 271 to determine a desired appliance schedule for one or more connected appliance activities. This appliance schedule is determined based on one or more of sleep schedule data, appliance stimulus data, user sensitivity data, energy data and/or pre-defined sleep quality goals. Pre-defined sleep quality goals, referred to herein as sleep goals, may include ideal total sleep time, time spent in a particular sleep stage, e.g. REM or N3 sleep, and associated costs of deviation. Sleep goals may be a pre-defined set of conditions for all users, or may be adjusted to some extent given predicted user requirements.

The scheduling unit 270 may include a sleep scheduling algorithm 272 to determine the optimal achievable schedule of user sleep stages, given available connected appliances and activities.

In certain embodiments, some modules, databases, and algorithms shown in FIG. 2 and described herein may not be required. For example, if a schedule is desired to improve the sleep quality of the user, without taking account of energy pricing (for example because price savings are not of interest or because the entire sleep period occurs within a period that does not have fluctuations in energy pricing), then features such as the energy database 260 may not be required.

Conversely, if a schedule is desired which optimises electricity pricing, without taking into account the user's sleep quality (for example because the user is not asleep or is away from home), then features such as the sleep sensor(s) 210, sleep database 215, environmental sensors 220, stimulus linking module 230, user sensitivity module 240, and sleep prediction algorithm 250 may not be required.

It will further be appreciated that any of the modules/units, algorithms, sensors, or databases may be combined with one or more other modules/units, algorithms, sensors, or databases. For example, the energy database 260, sleep database 215, appliance stimulus database 232, and/or user sensitivity database 242 may be combined into fewer databases or a single database.

Scheduling Process

Figure 3:
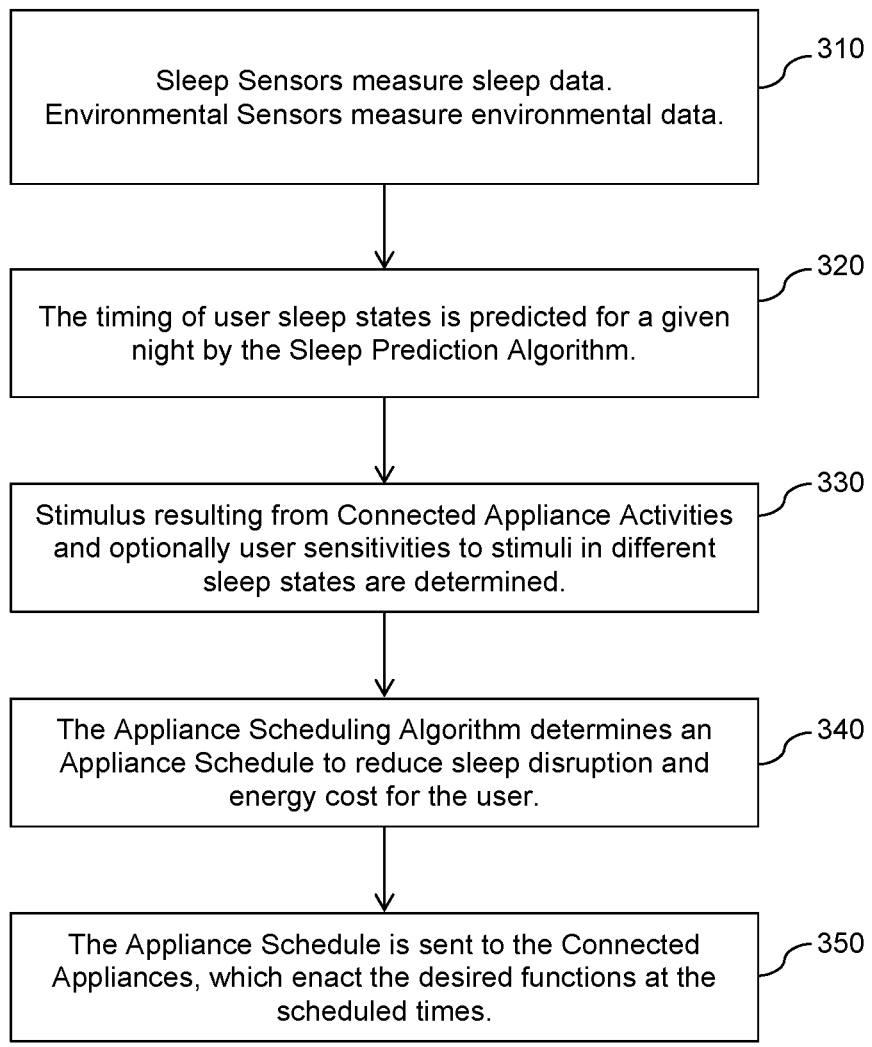
FIG. 3 illustrates a method for sleep stage dependent smart home scheduling.

Embodiments of the present invention provide a process for coordinating appliance activity and sleep stages. The process is depicted in FIG. 3 and is designed to improve sleep quality and reduce the cost of energy resulting from appliance activity. As discussed above, alternative embodiments are also envisaged which only optimise one of sleep quality, energy cost, or load balancing, or which optimise two or more of these features in combination.

Referring to FIG. 3, in step 310, the sleep sensors 210 (see FIG. 2) collect sleep data, and the environmental sensors 220 collect environmental data during one or more sleep states.

User sleep stages are determined by using the data collected by sleep sensors to monitor changes in user properties. For example, such properties may include (but are not limited to) heart rate variability, breathing, body temperature and/or movement. In the N1 light sleep stage (which is the first sleep stage a user experiences after falling asleep), it is typical for heart rate and breathing to begin to slow, and for body temperature to decrease. Heart rate and breathing slow down even further in deeper sleep stages, and heart rate tends to be more regular during deep sleep than in light sleep. Therefore these properties (or any other user properties indicative of user sleep state) may be monitored and evaluated in order to determine the sleep stages experienced by a user, including their timings.

In step 320, the timing of user sleep states is predicted for a given sleep period using the sleep prediction algorithm 250. The sleep prediction algorithm 250 extracts sleep data from the sleep database 215 and analyses it to determine the sleep schedule data some time into the future, such as the next night, or the rest of the current one. In some embodiments, this may be performed by taking average times of the onset of sleep stages in the user's sleep data. In some embodiments, separate averages may be taken for different combinations of factors which influence sleep stage timing. Such factors may include, but are not limited to, the time of sleep initiation, other sleep data from the current night's sleep, user mood, heart rate, tiredness, and amount and/or timing of exercise, food/drink consumption, and/or caffeine intake prior to sleeping.

In step 330, a stimulus resulting from connected appliance activities is determined, and optionally, user sensitivities to stimuli in different sleep states are determined. To determine the stimulus resulting from connected appliance activities, the stimulus linking algorithm 231 in the stimulus linking module 230 performs a correlation analysis of environmental data and appliance activity data. This analysis determines the appliance stimulus data, which is then stored in the appliance stimulus database 232. The user sensitivity data may be determined concurrently with the stimulus linking data, or may be determined before or after determination of the stimulus linking data. To determine the user sensitivity data, the user sensitivity algorithm 241 in the user sensitivity module 240 performs a correlation analysis of the changes in sleep state in the sleep data, correlated with the environmental data. The resulting determined user sensitivity data is then stored in the user sensitivity database 242.

In step 340, the appliance scheduling algorithm determines an appliance schedule to reduce sleep disruption and/or energy cost for the user. In preferred embodiments, the appliance schedule is determined so that the appliances run at times that minimise sleep impact. That is, the functions of various home appliances can be timed such that the effects on user sleep are optimized or reduced. This could be to avoid sleep disruption, such as by ensuring a washing machine spin cycle occurs when the user is in deepest sleep stage, or to rouse the user at an opportune time, such as prior to a scheduled alarm or when the user is experiencing a nightmare.

The appliance scheduling algorithm 271 in the scheduling unit 270 performs an optimisation function on the timing of the connected appliance activities given one or more of the sleep goals, appliance stimulus data, sleep schedule data and/or user sensitivity data. This optimisation function may output the appliance schedule which minimises the cost to user sleep (which may be measured by arousal likelihood in some embodiments) caused by connected appliance activity related stimuli.

An optimisation function which includes energy data may be applied if the cost to user sleep is low, e.g. below some threshold or zero. In other words, if there are a range of timings of connected appliance activities which result in the same or similar (best) user sleep condition, the timing with the best energy benefits such as the minimum energy cost and/or best load balancing outcomes may be selected.

Alternatively, the appliance scheduling algorithm 271 could optimise for energy related concerns as well as user sleep quality. For example, this may be achieved by converting the sleep impact (provided by the user sensitivity data) and the energy cost/load balancing concerns (provided by the energy data) into arbitrary units with pre-defined conversion rates based on an assessment of their relative importance to a generic user, or to the specific user.

The resulting appliance schedule comprises control data specifying a set of control actions for one or more connected appliances. The control data may comprise control instructions for the appliances, for example to activate or deactivate an appliance or set an operating mode, and may include control parameters such as a temperature setting (e.g. for a heating system), a program selection (e.g. for a washing machine) etc. Each control action in the control data is associated with timing information, e.g. specifying a time at which the action is to be performed, start/end times (or durations) for continuous appliance activities etc.

Optionally, the sleep scheduling algorithm 272 may use the user sensitivity data and/or known patterns of human sleep to design intentional user sleep adjustments which move the phases of the user's sleep to more advantageous times. For example, an adjustment may be determined so that deep sleep occurs in a time when energy is cheapest, thereby allowing energy intensive functions to be run at this time without disrupting sleep. Adjustments may be stored as further possible sleep schedules in the sleep schedule data. The appliance scheduling algorithm 271 may therefore be applied to each possible sleep schedule and an optimal combination may be selected.

The appliance and/or sleep schedule may be communicated to the user, for example via a smartphone or other user interface. In some embodiments, the system may allow the user to provide an input such as to accept or reject the new schedule, or by make adjustments to it. The scheduling unit may then re-calculate the schedule based on the user input.

Optionally, the system may further improve sleep quality by determining adjustments for user activities prior to sleep (e.g. to reduce caffeine intake, athletic activity, food/drink consumption, etc. before a sleep period), which are communicated to the user as described above. As above, the user may provide an input to accept, reject, or amend the proposed adjustments.

Optionally, a connected appliance 225 may have restrictions to the timing of its connected appliance activities. For example, a heating system may constrain its run time to 1-3 hours before the user wakes up. This may help to ensure that the room is still warm when the user awakes.

If multiple users may be affected by the same connected device activities, the sleep goals and/or other data of these multiple users may be taken into account. This may be to optimise the system to create the greatest benefit for multiple users. Optionally, the sleep cycles of multiple users in a location may be synchronised to maximize the benefit of connected appliance scheduling.

In step 350, the appliance schedule is sent to the one or more connected appliances 225, which implement the specified control actions at the scheduled times. Alternatively, the system may further include a central controller that controls the one or more connected appliances 225 to enact the one or more control actions at the scheduled times. For example, this may be achieved by the controller sending a control signal to a connected appliance 225 at the time when the scheduled activity should be performed.

In some embodiments, a connected appliance 225 may be a washing machine with controllable wash scheduling. The washing machine may be scheduled to operate during a period when the user is expected to be in a deep sleep cycle, thereby reducing the risk of disturbing the user's sleep. More refined control may also be available by scheduling the sub-processes of a connected appliance, such as by scheduling the sub-processes of a washing machine's wash cycle. For example, the spin cycle, which can be very loud and disruptive, may be scheduled such that it does not occur while a user is in a light sleep stage.

In some embodiments, a connected appliance 225 may be a heating system which may produce significant noise during the heating process. For example, this noise could be produced due to the expansion of pipes. Furthermore, the heating system, or any other temperature control system, could lead to temperatures which are too high or too low. This could negatively impact the user's sleep quality and/or may even wake the user. Therefore, in some embodiments, a heating system or other temperature control system could be scheduled to optimise temperatures for improving a user's sleep quality.

In some embodiments, a connected appliance 225 may be a dishwasher. The dishwasher schedule may be optimised in accordance with the user's sleep schedule and/or cheap electricity times. Furthermore, the dishwasher alarm that indicates the end of a dishwasher cycle could be controlled such that it does not produce sound while the user is asleep. This principle could also be applied to other types of appliances, such as to control the alarm that indicates the end of a washing machine cycle.

In some embodiments, a connected appliance 225 may be a fridge-freezer, such as a fridge-freezer with a compressor. The fridge-freezer may be scheduled to reduce impact on the user's sleep quality, for example by scheduling the compressor so that it does not run whilst the user is in a light sleep stage. This scheduling may also be optimised to take into account cheaper electricity times, in order to reduce energy costs.

Predictive and Dynamic Scheduling

The appliance schedules and sleep schedules described herein may be determined based off previous and/or current data, using a variety of techniques.

In some embodiments, the scheduling unit 270 may predictively determine an appliance and/or sleep schedule some time in advance of the a scheduled period, such as in advance of a particular night. This may be determined using previous environmental data, sleep data, and/or other relevant data. For example, the system may use data from multiple nights in order to determine "average" sleep patterns. This average may then be used to predictively generate an appliance schedule for subsequent nights. In addition to specifying timings for performing an appliance activity, an appliance schedule may further specify one or more settings for the appliance activity.

Alternatively or in combination, the scheduling unit 270 may determine or update a schedule dynamically, based on current data inputs such as current environmental data, appliance activity data, sleep data, and/or other relevant current data. For example, the system may use current sleep data to determine whether a user is falling asleep, changing sleep state, or awakening. Accordingly, the appliance scheduling algorithm 271 may determine and/or update a schedule for a connected appliance 225 to perform an activity in accordance with the time at which the user's sleep changes. For example, the system may suppress/delay a disruptive appliance activity (e.g. a washing machine spin cycle) if it detects the user entering a light sleep stage. As another example, if a user falls asleep while an appliance such as a TV, radio, or light is turned on, the system may control the appliance to turn off once the user has fallen asleep, by using the one or more sleep sensors 210 to determine the time at which this occurs. Conversely, a connected appliance 225 may be scheduled to turn on when the user awakens or when the user is in a light sleep stage. For example, connected appliances 225 such as a coffee machine and/or heating system may be scheduled to turn on at or around the time that the user wakes up. The appliance schedule may further specify a particular setting or combination of settings (e.g. volume, brightness, temperature, etc.) for the connected appliance 225 at the scheduled time. Accordingly, embodiments of the invention may help the user to wake up and/or otherwise assist the user by automating appliance activities.

In some embodiments, the above techniques may be combined such that a schedule which was predictively determined based on previous data is dynamically updated in response to current data. For example, if an appliance schedule was determined based on a predicted user sleep schedule some time in advance of the scheduled period, the appliance schedule may be dynamically updated during the scheduled period in response to differences between measured sleep data and the previously-predicted sleep schedule. For example, if a user falls asleep at a different time than previously predicted, the sleep prediction algorithm 250 may update the predicted sleep schedule, preferably including updated timings of different sleep stages. The appliance scheduling algorithm 271 may then dynamically update the appliance schedule in accordance with the new predicted sleep schedule.

Furthermore, if the user's sleep state changes unexpectedly, then an appliance activity may be re-scheduled accordingly. For example, if the current sleep data differs from the predicted sleep schedule, the system may update the predictively-determined appliance schedule. For example, if an appliance activity is scheduled to begin at a certain time, but at that time the system determines that the user has just changed to a lighter sleep state than previously predicted, the appliance scheduling algorithm 271 may update to cancel, postpone, or re-schedule the appliance activity.

Temperature Control

Some embodiments of the scheduling system provide for improved thermal control, by creating an appliance schedule for a heating and/or air conditioning appliance. The system can control factors such as which locations to heat, when to heat them, and/or to what temperature.

An appliance schedule, optionally including control of appliance activity settings such as a temperature setting, can be determined to optimise sleep and/or energy benefits, as described herein. Optionally, the system may control connected appliances in order to optimise the temperature for each sleep stage, by taking into account each sleep stage's different optimal thermal environment. As described herein, the system may further take into account the user's differing sensitivities during each sleep stage, and the schedule may be determined predictively, dynamically, or a combination thereof.

In some examples, thermal battery concepts may be applied by heating the user's house during a period of deep sleep when the noise from a heating system's pipes expanding will not be as disruptive. If energy data is also taken into account, cheaper heating may be provided when the user wakes up, without reducing the quality of their sleep.

System Architecture

Figure 4:
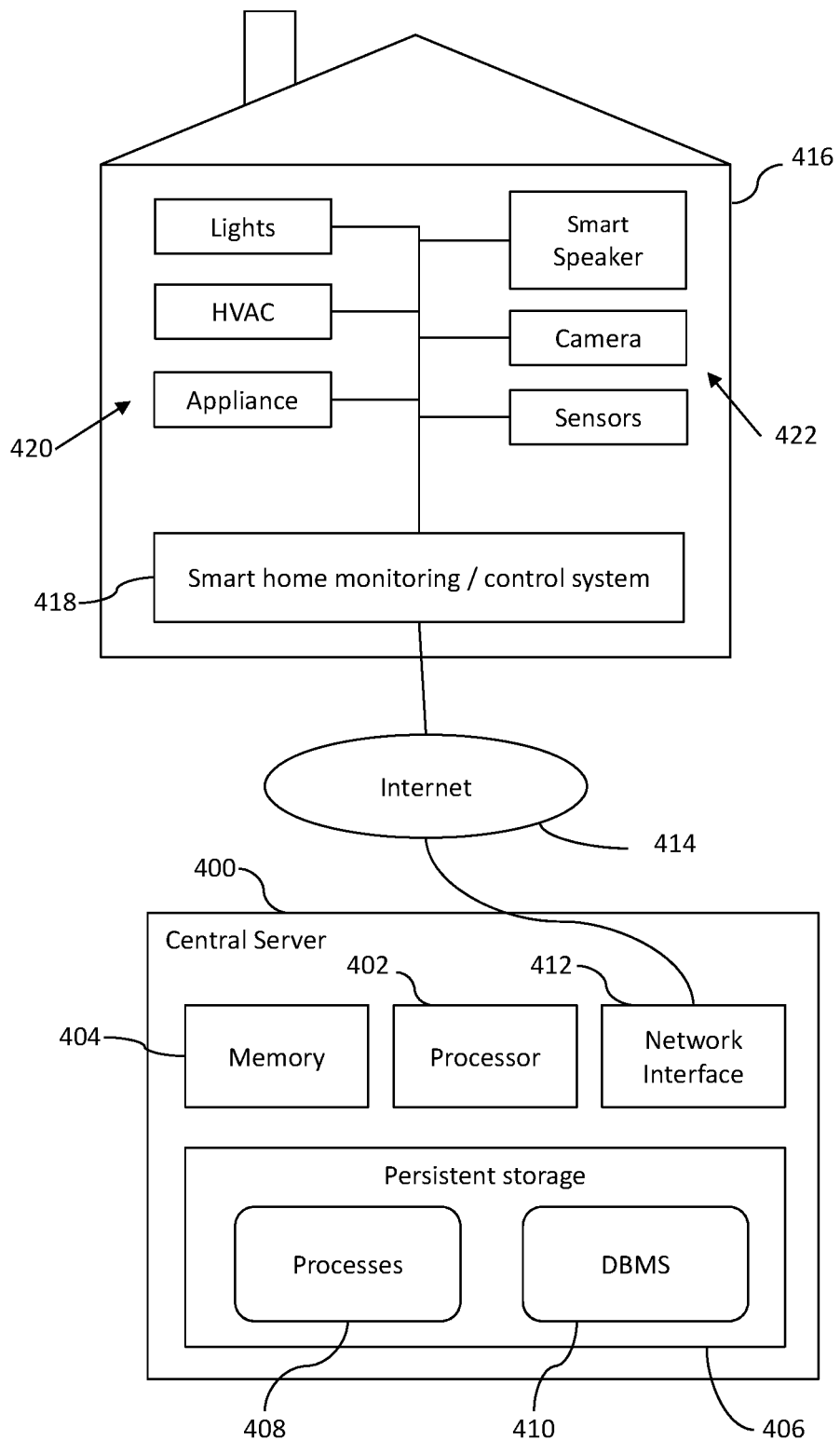
FIG. 4 illustrates components of a sleep stage dependent smart home control/scheduling system.

An example of a system for implementing described techniques is illustrated in FIG. 4. In this exemplary embodiment, the system is implemented as an internet based service with analysis/processing at a central location. The system includes a central server 400 for implementing functions of the smart home system. The server includes one or more processors 402 together with volatile/random access memory 404 for storing temporary data and software code being executed.

Persistent storage 406 (e.g. in the form of hard disk storage, optical storage, and the like) persistently stores software for performing various described functions, including a set of sleep stage and appliance schedule analysis, prediction, and control processes 408 (e.g. comprising the various algorithms 250, 231, 241, 271, 272 as shown in FIG. 2), and a database management system (DBMS) 410 for storing data used by the processes, including for example databases 215, 232, 242, 260 as shown in FIG. 2. The persistent storage 406 also includes other server software and data (not shown), such as a server operating system.

The server 400 will typically include other conventional hardware and software components as known to those skilled in the art.

A network interface 412 is provided for communication with other system components and in particular with a smart home 416 over a wide area network (typically comprising the Internet) 414. The smart home 416 includes a smart home monitoring and control system 418 (e.g. a local computing node or hub), which implements control schedules/actions and passes sensor data back to the central server 400.

The smart home monitoring/control system 418 is connected to a variety of smart devices throughout the smart home via a local network (e.g. including one or more wired and/or wireless networks). These are broadly divided into connected appliances 420 and sensor devices 422. Connected appliances 420 may, for example, include lighting, heating/ventilation/air-conditioning (HVAC) systems, washing machines, dryers, dishwashers, etc. Sensor devices 422 may include sleep sensors 210 and/or environmental sensors 220. For example, sensor devices may include smart speakers (or other devices with microphones), cameras, other sensors (e.g. temperature sensors), wearable fitness trackers and other examples of sleep sensors 210 and/or environmental sensors 220 described herein.

The smart home monitoring/control system 418 records data about the smart home based on information from the devices directly or from sensor devices 422, and transmits relevant data to the central server 400. The central server 400 performs analysis functions as described previously and generates one or more sleep and/or appliance schedules for transmission to the user or smart home 416. Optionally, the sleep and/or appliance schedule is output to a user who can approve, amend, or reject the schedule. If an appliance schedule is generated, the smart home monitoring/control system executes the appliance schedule by controlling controllable devices 420 in accordance with the schedule.

While a specific architecture is shown by way of example, any appropriate hardware/software architecture may be employed.

Functional components indicated as separate may be combined and vice versa. For example, the functions of server 400 may in practice be implemented by multiple separate server devices, e.g. by a cluster of servers. For example, the processes 408 and DBMS 410 may be hosted on different server devices. Also, the various functions may be divided between the smart home monitoring/control system 418 in the Smart Home and the central server 400 in any appropriate manner. In one example, all processing could be performed centrally, at server 400, with the various Smart Home devices directly connected to the Internet, removing the need for a separate computing node in the Smart Home.

In other alternative embodiments, the central server 400 and wide area network 414 may not be required, since the features of the central server 400 may instead be included locally in the smart home monitoring/control system 418.

It will be appreciated that methods described herein, for example with regards to FIGS. 1 and 3 and elsewhere, may be performed in a different order and/or some steps may be performed concurrently with other steps.

Although embodiments are sometimes described herein with references to night time scheduling, it will of course be appreciated that embodiments of the invention may also be used for other time periods. For example, some electricity tariffs offer cheaper electricity during one or more periods of the day, when there is lower demand due to consumers being away at the office. Accordingly, it is readily envisaged that the present invention could optimise appliance scheduling during these one or more daytime periods. For example, sleep quality and energy pricing could be optimised for a user who works night shifts and sleeps during the day. Alternatively, if a user is not asleep and/or is away from home during the day, energy pricing could be reduced by scheduling appliances to run during one or more off-peak daytime periods.

The above embodiments are described by way of example only. Many variations are possible without departing from the scope of the invention as defined in the appended claims.

The invention claimed is:

1. A computer-implemented method of controlling one or more appliances in a user environment, the one or more appliances in operation capable of causing environmental stimuli disruptive to a user's sleep, the method comprising:
receiving, during a first sleep period, data from one or more sensors indicative of a sleep state of the user;
generating, based on the received data, an appliance control schedule for controlling the one or more appliances during a second, later sleep period, wherein the control schedule specifies:
a plurality of control actions for controlling the one or more appliances to reduce sleep disruption due to the environmental stimuli caused by the appliances, and
timing information specifying times at which the control actions are to be performed; and
controlling the one or more appliances in dependence on the control actions and timing information specified by the control schedule during the second sleep period;
wherein generating the appliance control schedule comprises using the received data indicative of sleep state during the first sleep period to schedule operation of an appliance producing a sleep-disruptive environmental stimulus such that, during the second sleep period, the sleep-disruptive environmental stimulus occurs during a sleep stage corresponding to a deep sleep state.

2. A method according to claim 1, wherein the appliance control schedule comprises one or more of:
control instructions for the one or more appliances, optionally to activate or deactivate or set an operating mode of an appliance; and
control parameters for the one or more appliances, optionally to set an operating parameter of an appliance;
wherein controlling the one or more appliances optionally comprises transmitting the control instructions and/or control parameters to the one or more appliances.

3. A method according to claim 1, the method comprising:
based on the sensor data for the first time period, determining a sleep schedule of the user, the sleep schedule specifying a predicted sequence of sleep states over the second sleep period; and
generating the appliance control schedule in dependence on the predicted sleep schedule.

4. A method according to claim 1, comprising analysing the sensor data to perform one or more of:
classifying respective time intervals of the first sleep period into one of a predetermined set of sleep stages, and determining the predicted sleep schedule based on the classified sleep stages; and
determining respective sleep state timing information for a plurality of sleep stages occurring during the first sleep period, optionally wherein the sleep schedule comprises respective expected sleep stage timing information for a plurality of sleep stages during the second sleep period.

5. A method according to claim 1, comprising receiving from the one or more sensors a plurality of data sets, each comprising sleep data indicative of sleep states of the user during a respective sleep period; and determining the sleep and/or appliance control schedule based on the plurality of data sets.

6. A method according to claim 1, further comprising:
receiving environmental information relating to potentially sleep-disruptive stimuli in the user environment;
receiving appliance operation information relating to operation of the one or more appliances;
correlating the appliance operation information with the environmental information to identify at least one potentially sleep-disruptive stimulus associated with a given appliance; and
determining the one or more control actions or control schedule in dependence on the identified stimulus.

7. A method according to claim 1, wherein the control actions comprise one or more of: deactivating an appliance, controlling a time of operation of an appliance, or controlling an operating mode of an appliance, in dependence on the received data.

8. A method according to claim 1, wherein controlling one or more appliances comprises:
preventing or adjusting operation of an appliance to avoid or reduce a sleep-disruptive environmental stimulus during a sleep stage identified as corresponding to a light sleep.

9. A method according to claim 1, comprising evaluating a sleep impact of an appliance in dependence on an environmental stimulus produced by the appliance and a current or predicted sleep stage of the user, and determining the appliance control actions or schedule in dependence on the sleep impact.

10. A method according to claim 1, comprising, for one or more environmental stimuli caused by one or more appliances:
detecting the environmental stimulus using one or more environmental sensors;
analysing the sleep data to determine an effect of the environmental stimulus on the user sleep state, optionally by correlating detection of the environmental stimulus with changes in user sleep state; and
determining a user sensitivity to the stimulus based on the analysis;
the method preferably further comprising controlling the one or more appliances in dependence on the determined user sensitivity, optionally by selecting an appliance to be controlled based on the user sensitivity data and/or determining an appliance control action or schedule in dependence on the user sensitivity data.

11. A method according to claim 1, wherein environmental stimuli comprise one or more of: sound, light, and temperature.

12. A method according to claim 1, wherein control actions comprise one or more of:
disabling or altering an operating mode or schedule of a noise-generating appliance to reduce noise disruption;
disabling or altering an operating mode or schedule, or modifying a target temperature or temperature control schedule, of a heating, ventilation or air conditioning (HVAC) appliance.

13. A method according to claim 1, further comprising determining the control actions or schedule further in dependence on energy consumption and/or energy cost information the method optionally comprising determining an appliance control schedule by selecting appliance operation timings based on the sleep schedule and time-variable energy costs.

14. A method according to claim 1, further comprising:
outputting sleep schedule information to a user specifying proposed sleep adjustments to reduce sleep disruption due to appliance operation and/or allow appliance operation during times associated with reduced energy costs.

15. A method according to claim 1, further comprising determining the appliance control schedule using an optimisation function to determine timings of connected appliance activities given one or more of:
a determined sleep schedule;
one or more sleep goals;
appliance stimulus data defining environmental stimuli caused by appliances;
user sensitivity data indicating a user sensitivity to one or more stimuli; and
energy consumption and/or energy cost data.

16. A method according to claim 1, further comprising determining the appliance control schedule using an optimisation function to minimise a cost to user sleep caused by connected appliance activity related stimuli given a determined sleep schedule and appliance stimulus data defining environmental stimuli caused by appliances.

17. A system for controlling one or more appliances in a user environment, the one or more appliances in operation capable of causing environmental stimuli disruptive to a user's sleep, the system comprising at least one processor with associated storage storing instructions configured, when executed by the at least one processor, to perform operations including:
receiving, during a first sleep period, data from one or more sensors indicative of a sleep state of the user;
generating, based on the received data, an appliance control schedule for controlling the one or more appliances during a second, later sleep period, wherein the control schedule specifies:
a plurality of control actions for controlling the one or more appliances to reduce sleep disruption due to the environmental stimuli caused by the appliances, and
timing information specifying times at which the control actions are to be performed; and
controlling the one or more appliances in dependence on the control actions and timing information specified by the control schedule during the second sleep period;
wherein generating the appliance control schedule comprises using the received data indicative of sleep state during the first sleep period to schedule operation of an appliance producing a sleep-disruptive environmental stimulus such that, during the second sleep period, the sleep-disruptive environmental stimulus occurs during a sleep stage corresponding to a deep sleep state.

18. A non-transitory computer-readable medium comprising software code adapted, when executed on a data processing apparatus, to perform a method of controlling one or more appliances in a user environment, the one or more appliances in operation capable of causing environmental stimuli disruptive to a user's sleep, the method comprising:
receiving, during a first sleep period, data from one or more sensors data indicative of a sleep state of the user;
generating, based on the received data, an appliance control schedule for controlling the one or more appliances during a second, later sleep period, wherein the control schedule specifies:
a plurality of control actions for controlling the one or more appliances to reduce sleep disruption due to the environmental stimuli caused by the appliances, and
timing information specifying times at which the control actions are to be performed; and
controlling the one or more appliances in dependence on the control actions and timing information specified by the control schedule during the second sleep period;
wherein generating the appliance control schedule comprises using the received data indicative of sleep state during the first sleep period to schedule operation of an appliance producing a sleep-disruptive environmental stimulus such that, during the second sleep period, the sleep-disruptive environmental stimulus occurs during a sleep stage corresponding to a deep sleep state.

19. A method according to claim 1, comprising coordinating operation of the one or more appliances with the sleep schedule, the coordinating preferably comprising selecting operation timings and/or operational parameters for one or more appliances in dependence on the sleep schedule.

* * * * *